(12) United States Patent
Newberry et al.

(10) Patent No.: US 9,635,858 B2
(45) Date of Patent: May 2, 2017

(54) PESTICIDE AND A METHOD OF CONTROLLING A WIDE VARIETY OF PESTS

(71) Applicant: GOWAN COMERCIO INTERNACIONAL E SERVICOS LIMITADA, Madeira (PT)

(72) Inventors: George David Newberry, Boise, ID (US); Oakford George Bain, Yuma, AZ (US); Chad Douglas Dyer, Yuma, AZ (US); Dario Sterzi, Guardia Sanframondi (IT)

(73) Assignee: Gowan Comercio Internacional E Servicos Limitada, Madiera (PT)

( * ) Notice: Subject to any disclaimer, the term of this patent is extended or adjusted under 35 U.S.C. 154(b) by 0 days.

(21) Appl. No.: 13/705,274

(22) Filed: Dec. 5, 2012

(65) Prior Publication Data

US 2013/0203842 A1 Aug. 8, 2013

Related U.S. Application Data

(60) Provisional application No. 61/567,317, filed on Dec. 6, 2011.

(51) Int. Cl.
*A01N 43/90* (2006.01)
*A01N 37/00* (2006.01)
*A01N 25/30* (2006.01)

(52) U.S. Cl.
CPC ............ *A01N 43/90* (2013.01); *A01N 25/30* (2013.01); *A01N 37/00* (2013.01)

(58) Field of Classification Search
None
See application file for complete search history.

(56) References Cited

U.S. PATENT DOCUMENTS

| 5,001,146 | A | 3/1991 | Carter et al. |
| 5,346,698 | A | 9/1994 | Abercrombie |
| 5,409,708 | A | 4/1995 | Locke et al. |
| 6,733,802 | B1 | 5/2004 | Moorty et al. |
| 2004/0037904 | A1 | 2/2004 | Hakansson |
| 2005/0244445 | A1 | 11/2005 | Anderson |
| 2009/0192040 | A1* | 7/2009 | Grobler .................. 504/313 |
| 2009/0258950 | A1 | 10/2009 | Knoblauch |

FOREIGN PATENT DOCUMENTS

| CN | 1112106 C | 6/2003 |
| EP | 0862861 | 9/1998 |

* cited by examiner

*Primary Examiner* — San-Ming Hui
*Assistant Examiner* — Andrew Lee
(74) *Attorney, Agent, or Firm* — Norris McLaughlin & Marcus PA

(57) ABSTRACT

A pesticidal composition including at least one substance derived from *Azadirachta indica* plant, at least one metal salt of a fatty acid and at least one excipient. The present disclosure also relates to a kit including the pesticidal composition. The present disclosure further relates to use of pesticidal composition/kit in controlling a wide variety of pests.

25 Claims, 2 Drawing Sheets

PESTICIDE AND A METHOD OF CONTROLLING A WIDE VARIETY OF PESTS

CROSS-REFERENCE TO RELATED APPLICATIONS

Figure 1:
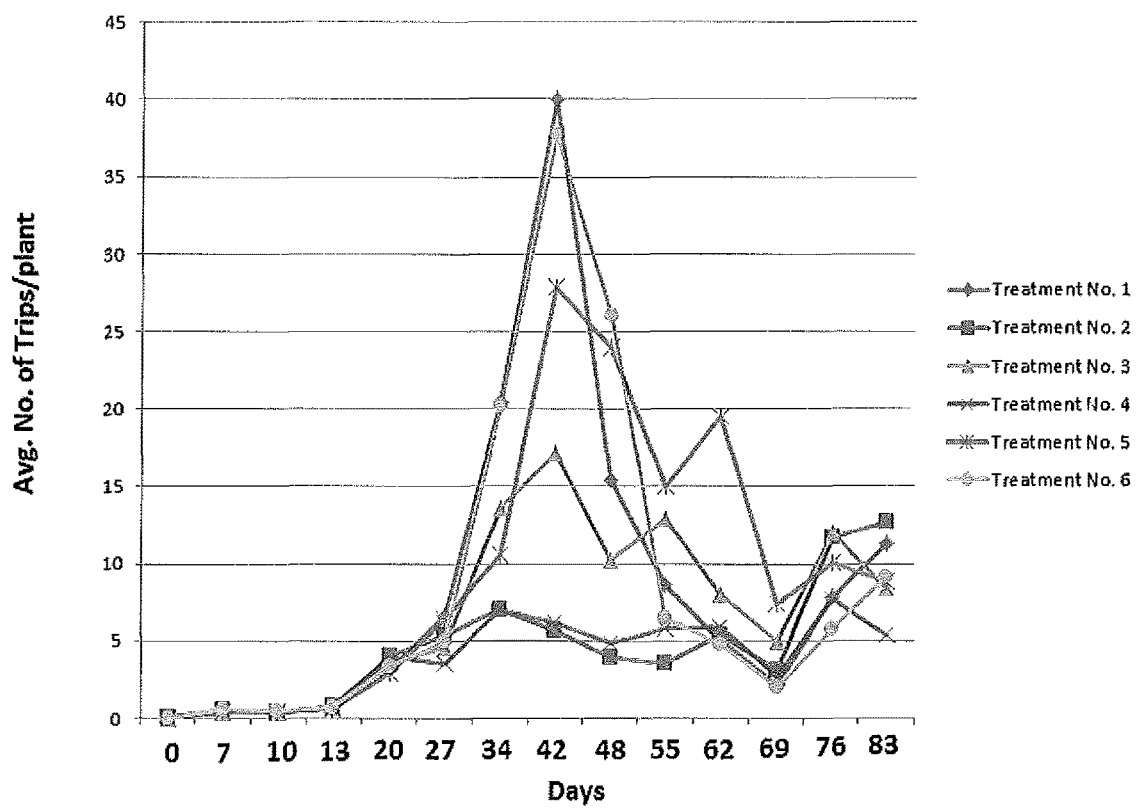

This application claims priority to U.S. Provisional Application No. 61/567,317 filed Dec. 6, 2011, incorporated by reference in its entirety.

FIELD OF THE DISCLOSURE

The present disclosure relates to a pesticide, use of a pesticide and a method of controlling a wide variety of pests. The present disclosure also relates to a method for treating agricultural products for insects, microorganisms and other infestations.

BACKGROUND

A pest is an organism which is detrimental to humans or human concerns. Pests include insects, plant pathogens, weeds, molluscs, birds, mammals, fish, nematodes (roundworms) and microbes.

Typically, pests are classified into insects, mites, nematodes and gastropods. Pesticides are substances or mixture of substances intended for preventing, destroying, repelling or mitigating any pest. A pesticide may be a chemical agent, a biological agent (such as a virus or bacterium), an antimicrobial, a disinfectant or a device used against any pest.

Pesticides are categorized into four main substituent chemicals: herbicides, fungicides, insecticides and bactericides. Pesticides can be classified by target organism, chemical structure and physical state. Pesticides can also be classed as inorganic, synthetic, or biological (bio-pesticide). Bio-pesticides include microbial pesticides and biochemical pesticides. These include pyrethroids, rotenoids and nicotinoids. Pesticides can also be classified based upon their biological mechanism function or application method. Most pesticides work by poisoning the pests.

An insecticide is a pesticide used against insects. They include ovicides and larvicides, used against the eggs and larvae of insects respectively. Insecticides are classified in several different ways. Typically, they are classified as systemic insecticides, contact insecticides, natural insecticides, plant-incorporated protectants (PIPS), inorganic insecticides and organic insecticides. The commonly known insecticides include: i) organochlorides such as DDT, aldrin, chlordane, chlordecone, heptachlor, methoxychlor, pentachlorophenol and the like; ii) organophosphates such as acephate, azinphos-methyl, bensulide, chlorethoxyfos, chlorpyrifos, diazinon, dimethoate, disulfoton, ethoprop, fenamiphos, parathion, trichlorfon and the like; iii) pyrethroids such as allethrin, bifenthrin, cyhalothrin, lambda-cyhalothrin, cypermethrin, cyfluthrin, prallethrin, transfluthrin and the like, iv) carbamates such as aldicarb, bendiocarb, carbofuran, carbaryl, dioxacarb, fenobucarb, fenoxycarb, isoprocarb, methomyl and the like.

Further, various plant derived insecticides are known such as anabasine, annonin, asimina, caffeine, carapa, cinnamaldehyde, citral, deguelin, eugenol, myristicin, azadirachtin, *nicotiana rustica* (nicotine) *peganum harmala, quassia*, and the like.

*Azadirachta indica* (Neem) is a tree of the mahogany family Meliaceae. It is one of the two species in the genus *Azadirachta* and is native to India, Pakistan, Bangladesh, Iran and grows in tropical and semi-tropical regions.

Neem oil typically contains nimbin, nimbinin and nimbidin. The seeds of neem contain a complex secondary metabolite known as azadirachtin.

Various parts of the neem tree have long been used in India for their medicinal properties such as anthelmintic, antifungal, antidiabetic, antibacterial, antiviral, contraceptive and sedative. Neem is also used for the treatment of urinary disorders, diarrhoea, fever, bronchitis, skin diseases, septic sores, infected burns, hypertension and inflammatory diseases.

Although all parts of the neem tree appear to have natural resistance to pests and diseases, the seeds appear to have the greatest resistance. Formulations and extracts of the seeds are effective against many species of crop pests, including gypsy moths, Japanese beetles, aphids, tobacco budworins and boll weevils.

Azadirachtin

Azadirachtin is a tetranortriterpenoid botanical insecticide of the liminoid class extracted from the neem tree (*Azadirachta indica*). It is a highly oxidized tetranortriterpenoid which boasts of a plethora of oxygen functionality and comprising an enol ether, acetal, hemiacetal, and tetra-substituted oxirane as well as a variety of carboxylic esters.

Structure

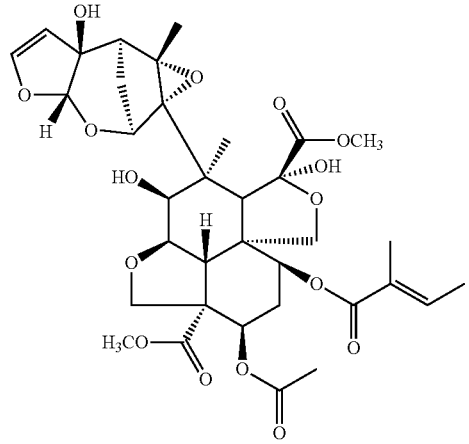

Azadirachtin is biodegradable (it degrades within 100 hours when exposed to light and water) and shows very low toxicity to mammals (the $LD_{50}$ in rats is >3,540 mg/kg making it practically non-toxic).

Mode of Action of Azadirachtin:

Azadirachtin is structurally similar to insect hormone "ecdysones". These hormones typically control the process of metamorphosis when the insects pass from larva to pupa to adult. Azadirachtin mainly acts as an "ecdysone blocker". It blocks the insect's production and release of vital hormones. As a result, insects cannot molt. Azadirachtin is also known to disturb mating and sexual communication of insects, repel larvae and adults, deter females from laying eggs, sterilize adults and deter feeding.

It is known in the prior art that compositions containing fatty acid ester salt are useful insecticides. The potassium salt of a fatty acid causes cuticle disruption of insects.

Some representative patent documents which disclose insecticide compositions containing either fatty acid ester salt per se or Azadirachtin as an active ingredient per se are discussed herein below.

European Patent No. 0862861 discloses a composition for killing thrips which comprises i) at least one fatty acid ester selected from the group consisting of glycerin diacetomonolaurate, glycerin monocaprylate, glycerin mono/dilinolate, sorbitan oleate, diglycerin oleate, propylene glycol monooleate; and ii) a non-ionic surfactant such as polyoxyethylene alkyl ether.

U.S. Pat. No. 5,346,698 discloses a composition comprising avermectins and related compounds such as abamectin in combination with one or more substituted or unsubstituted, saturated or unsaturated fatty acids or their salts.

US20050244445 discloses an insecticidal composition comprising i) at least one essential oil selected from the group consisting of corn mint oil, cedar oil, cinnamon oil, citronella oil, clove oil, corn oil, garlic oil, lemongrass oil, linseed oil, peppermint oil, rosemary oil, soybean oil, neem oil, thyme oil, orange oil, lemon oil, lime oil, grapefruit oil, tangerine oil, D-limonene, eugenol, geraniol, and palmarosa oil; and ii) soap which comprises potassium salts of fatty acids.

U.S. Patent No. 20090258950 discloses an insecticidal composition comprising: (a) 0.1-2.0% of potassium salts of fatty acids as an emulsifier; (b) 0.1-2.4% horticultural oil; (c) 0.1-1.2% cinnamaldehyde or cinnamon oil equivalent; and (d) 0.1-1.2% eugenol.

U.S. Pat. No. 5,001,146 discloses a storage-stable pesticide composition comprising a neem seed extract solution containing azadirachtin wherein the solution is characterized as having at least 50% by volume of aprotic solvent and less than 15% by volume of water said solution being non-degrading to azadirachtin U.S. Pat. No. 5,409,708 discloses a fungicide formulation comprising a fungicidally effective amount of clarified neem oil which has less than 1.0 weight percent of azadirachtin.

U.S. Pat. No. 6,733,802 discloses an emulsion comprising a biologically effective amount of azadirachtin in an essential oil and a surface active agent, wherein said emulsion is made from naturally occurring materials and is devoid of synthetic compounds.

None of the compositions disclosed in the prior art patent documents are able to control a wide variety of pests in an effective way. Furthermore, none of the patent document discloses a synergistic pesticidal composition containing a combination of the substance derived from *Azadirachta indica* plant and non-plant based material which is economically efficient and ecologically safe.

Commercially available insecticides commonly comprise active ingredients or poisons which are not only toxic to the target insect pests, but are also toxic to humans, if used in relatively confined environments and delivered as aerosol sprays. Various undesirable side effects may include immediate or delayed neurotoxic reactions and/or suffocation. Even the noxious odor of such materials can cause headaches or upset stomach in some individuals. These adverse side effects are exacerbated when such compositions come in contact with persons of increased sensitivity.

Despite the use of known pesticidal agents and compositions, there still exists a need for an economically efficient and ecologically safe insect control composition. The growing outcry against the use of hazardous insecticidal compounds has necessitated a need for a novel pest control method and/or insecticidal composition which can reduce the amount of pesticides necessary to obtain acceptable levels of control. Researchers have experimented with various combinations of various constituents as one approach to identify compositions which have desirable insecticidal characteristics. However, the probability of finding a combination with synergistic effects by this approach is very minimal.

In view of the above, there is envisaged in accordance with the present disclosure an environmentally safe synergistic pesticidal composition which is effective at lower dose.

OBJECTS OF THE DISCLOSURE

Some of the objects of the present disclosure are as follows:

It is an object of the present disclosure to provide a pesticide.

It is another object of the present disclosure to provide a pesticide composition which is highly effective against a wide variety of pests found on food and forage crops.

It is still another object of the disclosure to provide a pesticide composition which provides a long lasting effect with lower incidence of insect resistance.

It is a further object of the present disclosure to provide a process for the preparation of the pesticidal composition.

It is still further object of the present disclosure to provide an effective method for preventing and/or controlling a wide variety of pests such as mites, psylla, aphids, thrips, white fly and the like.

These and other objects of the present disclosure are to a great extent dealt in the disclosure.

In accordance with one aspect of the present disclosure there is provided a pesticidal composition comprising:
   i. at least one substance derived from *Azadirachta indica* plant;
   ii. at least one metal salt of a fatty acid; and
   iii. at least one excipient.

Typically, the substance is selected from the group comprising powder, extract and oil derived from *Azadirachta indica* plant material and azadirachtins.

Typically, the metal salt of a fatty acid is at least one selected from the group consisting of a potassium salt of a fatty acid, a sodium salt of a fatty acid, a calcium salt of a fatty acid, a magnesium salt of a fatty acid, an aluminium salt of a fatty acid and a manganese salt of a fatty acid, preferably, a potassium salt of a fatty acid.

Typically, the proportion of the substance derived from *Azadirachta indica* plant and the metal salt of a fatty acid ranges between 3000:1 and 1:3000, preferably 100:1 and 1:100. Most preferably, the proportion of the substance derived from *Azadirachta indica* plant and the metal salt of a fatty acid ranges between 50:1 and 1:50.

Typically, the amount of the metal salt of a fatty acid ranges between 0.01 w/w % and 30.0 w/w %.

Typically, the pesticidal composition of the present disclosure further comprises at least one oil selected from the group consisting of isopropyl myristate, myristyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, ethylhexyl cocoate, dicaprylyl carbonate, cetearyl isononanoate, oleyl erucate, erucyl oleate, erucyl erucate, octyldodecanol, polydecenes, squalane, dicaprylyl ether, triisostearine, butylene glycol dicaprylate, caprylic/capric triglyceride, vegetable oil, olive oil, sunflower oil, soybean oil, peanut oil, rapeseed oil, sesame oil, mustard oil, almond oil, palm oil, raw coconut oil, paraffin oil, mineral oil, flaxseed oil, palm kernel oil, caster oil, wheat germ oil, grape seed oil, thistle oil, silicon oils, lanolin oil, avocado oil and macadamia oil.

Typically, the excipient is at least one selected from the group consisting of vehicles, alkalizing agents, acidifying agents, dispersing agents, wetting agents, binding agents, emulsifiers, defoamers, wax and stabilizers.

Typically, the composition is in the form selected from the group consisting of aerial sprays, directly sprayable solutions, powders, suspensions, dispersions, emulsions, oil dispersions, pastes and water dispersible granules.

In accordance with another aspect of the present disclosure there is provided a method for controlling pests; said method comprising the following steps:
 i. preparing a composition comprising: at least one substance derived from *Azadirachta indica* plant, at least one metal salt of a fatty acid and at least one excipient; and
 ii. contacting an infested area with the composition by applying a pesticidal effective amount of said composition thereon.

Typically, the metal salt of a fatty acid is at least one selected from the group consisting of a potassium salt of a fatty acid, a sodium salt of a fatty acid, a calcium salt of a fatty acid, a magnesium salt of a fatty acid, an aluminium salt of a fatty acid and a manganese salt of a fatty acid, preferably, a potassium salt of a fatty acid.

In accordance with another aspect of the present disclosure there is provided a kit comprising;
 i. component A comprising at least one substance derived from *Azadirachta indica* plant;
 ii. component B comprising at least one metal salt of a fatty acid selected from the group consisting of a potassium salt of a fatty acid, a sodium salt of a fatty acid, a calcium salt of a fatty acid, a magnesium salt of a fatty acid, an aluminium salt of a fatty acid and a manganese salt of a fatty acid; and
 iii. at least one packaging material for packaging of the components (A) and (B);

In accordance with one of the embodiments of the present disclosure the components A and for B of the kit further comprises at least one excipient selected from the group consisting of vehicles, alkalizing agents, acidifying agents, dispersing agents, wetting agents, binding agents, emulsifiers, oils, wax, defoamers and stabilizers.

Typically, the substance is selected from the group comprising powder, extract and oil derived from *Azadirachta indica* plant material and azadirachtins.

Typically, the oil at least one selected from the group consisting of isopropyl myristate, myristyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oeyl oleate, ethylhexyl cocoate, dicaprylyl carbonate, cetearyl isononanoate, oeyl erucate, erucyl oleate, erucyl erucate, octyldodecanol, polydecenes, squalane, dicaprylyl ether, triisostearine, butylene glycol dicaprylate, caprylic/capric triglyceride, vegetable oil, olive oil, sunflower oil, soybean oil, peanut oil, rapeseed oil, sesame oil, mustard oil, almond oil, palm oil, raw coconut oil, paraffin oil, mineral oil, flaxseed oil, palm kernel oil, caster oil, wheat germ oil, grape seed oil, thistle oil, silicon oils, lanolin oil, avocado oil and macadamia oil.

In another aspect of the present disclosure, there is provided a method for controlling pests using the kit of the present disclosure by applying the components using at least one technique selected from the group consisting of applying the component A before the application of the component B, applying the component A after the application of the component B, simultaneous application of the components A and B and combining the components A and B before the application.

In yet another aspect of the present disclosure the composition or the kit is useful for controlling a wide variety of insect pests on crops/vegetables/fruit/nuts/turf/ornamental/perennial plants/animals plant selected from the group consisting of Blackberry, Blueberry, Cane berries, Currant, Elderberry, Gooseberry, Huckleberry, Loganberry, Raspberry (black and red), Strawberries, Boysenberry, Olallieberry Garlic, Leek, Onion (dry bulb, green and Welch), Shallot, Sugarbeet, Barley, Buckwheat, Corn, Millet (pearl and Proso), Oats, Popcorn, Rice, Rye, Sorghum (milo), Teosinte, Triticale, Wheat, Wild rice, Calamondin, Citrus citron, Citrus hybrids, Grapefruit, Kumquat, Lemon, Lime, Mandarin (tangerine), Orange (sour and sweet), Pummelo, Satsuma mandarin, White Sapote, Uniq Fruit, Chayote, Chinese waxgourd, Citron melon, Cucumber, Gherkin, Gourd (edible), Muskmelon, Pumpkin, Squash (summer and winter), Watermelon, Alfafla, Clover, Trefoil or Vetch, Eggplant, Groundcherry, Pepino, Pepper (including bell pepper, chili pepper, cooking pepper, pimento, sweet pepper), Tomatillo, Tomato, Allspice, Angelica, Anise (anise seed and star), Annatto (seed), Balm (lemon balm), Basil, Borage, Burnet, Camomile, Caper buds, Caraway, Caraway (black), Cardamom, Cassia bark, Cassia buds, Catnip, Celery, Celery seed, Chervil (dried), Chive, Chinese Chive, Cinnamon, Clary, Clove buds, Coriander (cilantro or Chinese parsley—leaf), Coriander (cilantro—seed), Costmary, Culantro (leaf and seed), Cumin, Curry (leaf), Dill (dillweed and seed), Fennel (common, Florence), Fenugreek, Grains of paradise, Horehound, Hyssop, Juniper berry, Lavender, Lemongrass, Lovage (leaf and seed), Mace, Marigold, Marjoram, Mustard (seed), Nasturtium, Nutmeg, Parsley (dried), Pennyroyal, Pepper (black and white), Poppy (seed), Rosemary, Rue, Saffron, Sage, Savory, Sweet bay (bay leaf), Tansy, Tarragon, Thyme, Vanilla, Wintergreen, Woodruff, Wormwood, Bean, Broad Bean, Chickpea, Guar, Jackbean, Lablab bean, Lentil, Pea, Pigeon Pea, Soybean, Sword bean, Amaranth, Arugula, Broccoli, Broccoli raab (rapini), Brussels Sprouts, Cabbage, Cauliflower, Cardoon, Cavalo broccolo, Celery, Chinese Broccoli (gai ion), Chinese Cabbage (bok choy, Napa), Chinese mustard Cabbage (gai choy), Chinese Celery, Celtuce, Chervil, Chrysanthemum (edible—leaved, Garland), Collards, Corn salad, Cress (garden, upland), Dandelion, Dock (sorrel), Endive (escarole), Fennel (florence), Kale, Kohlrabi, Lettuce (head and leaf), Mizuna, Mustard Greens, Mustard Spinach, Orach, Parsley, Purslane (garden, winter), Radicchio (red chicory), Rape Greens, Rhubarb, Spinach, Spinach (New Zealand, vine), Swiss Chard, Turnip Greens, Asparagus, Avocado, Banana, Coffee, Cocoa, Cranberry, Fig, Globe artichoke, Grape, Hops, Kiwifruit, Mango, Mushroom, Okra, Olives, Papaya, Pawpaw, Peanut, Persimmon, Pineapple, Pomegranate, Strawberry, Tea, Water chestnut, Watercress, Apple, Crabapple, Loquat, Mayhaw, Quince, Oriental Pear, or Pear (Cornice), Arracacha, Arrowroot, Artichoke (Jerusalem, Chinese), Beet (garden, sugar), Burdock (edible), Canna (edible), Carrot, Cassava (bitter and sweet), Celeriac (celery root), Chayote (root), Chervil, (turnip—rooted), Chicory, Chufa, Dasheen (taro), Ginger, Ginseng, Horseradish, Leren, Oriental Radish (daikon), Parsley (turnip—rooted), Parsnip, Potato, Radish, Rutabaga, Salsify (oyster plant, black, Spanish), Skirret, Sweet potato, Tanier, Turmeric, Turnip, Yam bean (jicama, manoic pea), Yam (true), Apricot, Chemy (sweet and tart), Nectarine, Peach, Plum (Chickasaw, Damson, Japanese), Plumcot, Prune, Almond, Beech nut, Brazil nut, Butternut, Cashew, Chestnut, Chinquapin, Filbert (hazelnut, Hickory nut, Macadamia nut (bush nut), Pecan, Walnut (black and English), Pistachios, Black Sapote, Canistel, Mamey Sapote, Mango, Sapodilla, Star Apple, Guava, Feijoa, Jaboticaba, Wax Jambu, Star Fruit, Passion Fruit, Acerola, Lychee, Longan, Spanish Lime, tangelo, Rambutan, Pulasan, Sugar Apple, Atemoya, Custard Apple, Chemmoya, Ilama, Soursop, Biriba, Amaranthus, Aster, Azalea, Ferns, Fuschia, Caladium, Carnation, Chrysanthemum, Dahlia, Daisy, Lilies, Ivy, Ficus, Gardenia, Impatiens, Iris, Jasmine, Lilac, Marigold, Philodendron, Poinsettia, Rose, Zinnia, Ash, Birch, Cedar, Cyprus, Dogwood, Fir, Elm, Juniper, Maple, Oak, Pine, Spruce, Alfalfa, Canola, Cotton, Tobacco, Christmas Tree, Oilseed Rape, Bushberry, cucurbit, legume and Beechnut.

In one more aspect of the present disclosure the composition or the kit is useful in controlling at least one pest selected from the group consisting of Adelgid, ants, Aphids, armyworm, Balsam woolly adelgid, Blossom thrips on African violets, Broad mites, buck moth larvae, campylomas, Chinch bugs, Citrus rust mites, Conifer and pine needle scale, Cooley Spruce gall adelgid, cutworm, Earwig, elm leaf beetle larvae, Euonymous scale, European red mites, fleahopper, fleas, fungus gnat, Green apple aphids, Green peach, greenbug, grubs, gypsy moth eggs and larvae, Gypsy moth, Hemlock woolly adelgid, Japanese beetle, lace bugs, Leafhopper, Leafminer (Dipteran), leafroller, looper, Lygus bug, Mealy Bug, Mite, Mole crickets, Pacific mites, Pea aphid, peach twig borers, peach tree borers, Psylla, pear Psylla, pear slug (sawfly larvae), phylloxera, plant bug, powdery mildew, psyllid, Rosy Apple Aphid, Russet mites, rust mites, San Jose scale, sawfly larvae, scale, shore fly, sod webworms, spider mite, Spruce spider mite on conifers, stink bug, Tent caterpillar, Thrips, True Bugs, two spotted mites, variegated leafhoppers, walnut husk fly, Weevil, western flower thrip, Western grape aphids, White apple leafhoppers, Whitefly, Willamette mites, apple maggot, banded grape bug, black pecan aphid, blueberry maggot, cherry fruit flies, codling moth, Colorado potato beetle, dock sawfly, elm spanworm, European corn borer, European sawfly, fire worms, fruit worms, grape berry moth, grape cane borer, grape leaf folder, green fruit worm, hickory shuck worm, lygocoris bug, naval orange worm, orange tortix, oriental fruit moth, pecan nut casebearer, pine tip moth, plum curculio, red humped caterpillar, rose chafer, spanworm, spotted wing drosophila, strawberry root weevil adult, syneta beetle, western grape leaf skeletonizer, western tussock moth, black cherry aphid and asian citrus psyllid.

BRIEF DESCRIPTION OF THE ACCOMPANYING DRAWING

FIG. 1—illustrates average thrips count per treatment; wherein
1—Treatment No. 1, 2—Treatment No. 2, 3—Treatment No. 3, 4 —Treatment No. 4, 5—Treatment No. 5 and 6—Treatment No. 6.

Figure 2:
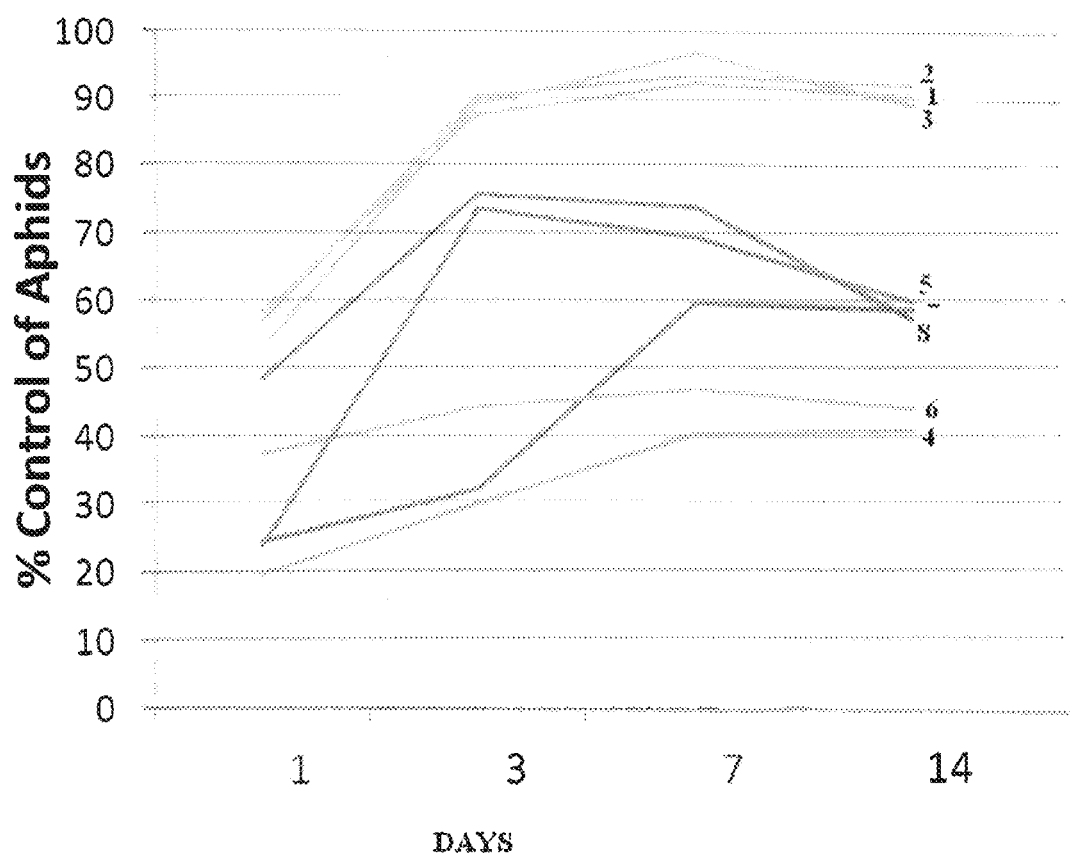

FIG. 2—illustrates percent control of aphids by various combinations of the substance derived from *Azadirachta indica* plant and the potassium salt of a fatty acid; wherein
1—Treatment No. 1, 2—Treatment No. 2, 3—Treatment No. 3, 4 —Treatment No. 4, 5—Treatment No. 5, 6—Treatment No. 6, 7—Treatment No. 7 and 8—Treatment No. 8.

DETAILED DESCRIPTION

In order to overcome the drawbacks associated with the known pesticides, it is envisaged in accordance with the present disclosure an environmentally safe synergistic pesticidal composition which is effective at a lower dose.

The inventors of the present disclosure focused on the development of synergistic pesticidal compositions containing at least one substance derived from the *Azadirachta indica* plant and at least one chemical compound such as a metal salt of a fatty acid. The commercially available samples of *Azadirachta indica* were collected from India and subcontinent.

The inventors of the present disclosure have come across several surprising findings during the ongoing field trials on various crops, the distinct one being the synergistic nature of the composition of the present disclosure, when applied by the methods envisaged in the present disclosure.

After conducting several trials, the inventors of the present disclosure developed a synergistic pesticidal composition containing at least one substance derived from *Azadirachta indica* plant and at least one chemical compound such as a metal salt of a fatty acid. The particular proportions of the constituents and the method of application of the composition of the present disclosure produces a synergistic effect. It is also found that the synergistic composition of the present disclosure is effective at lower doses and is environmentally safe.

The synergistic effect of the composition of the present disclosure, may be attributed to the fact that each of the pesticidal agent acts through different modes of action at different stages of the life cycle of insects.

Azadirachtin being an "ecdysone blocker" blocks the insect's production and release of vital hormones while the potassium salt of a fatty acid causes cuticle disruption.

In accordance with the present disclosure there is provided a pesticidal composition comprising:
  i) at least one substance derived from *Azadirachta indica* plant;
  ii) at least one metal salt of a fatty acid; and
  iii) at least one excipient.

The substance derived from *Azadirachta indica* plant includes powder, crude, extract, oil, active constituents obtained from leaves, seeds, root, bark or any combinations thereof. The substance derived from *Azadirachta indica* plant is an active constituent and is at least one selected from the group consisting of azadirachtin, namely azadirachtin A and azadirachtin B.

The amount of azadirachtin in the composition is adjusted such that when applied its amount ranges between 0.00001 lbs ai per acre and 1.0 lbs ai per acre.

In one of the embodiments of the present disclosure, the metal salt of a fatty acid such as a potassium salt of a fatty acid, a sodium salt of a fatty acid, a calcium salt of a fatty acid, a magnesium salt of a fatty acid, an aluminium salt of a fatty acid and a manganese salt of a fatty acid is used in combination with the substance derived from *Azadirachta indica*. Particularly, potassium salt of a C4 to C28 fatty acid is used. The amount of the potassium salt of a fatty acid used is in the range of about 0.01 w/w % to about 30.0 w/w %.

In one of the embodiment of the present disclosure the proportion of the substance derived from *Azadirachta indica* plant and the metal salt of a fatty acid ranges between 3000:1 and 1:3000, preferably 100:1 and 1:100.

In one of the most preferred embodiment of the present disclosure the proportion of the substance derived from

*Azadirachta indica* plant and the metal salt of a fatty acid ranges between 50:1 and 1:50.

In one of the embodiment of the present disclosure the pesticidal composition further comprises at least one oil selected from the group consisting of isopropyl myristate, myristyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, ethylhexyl cocoate, dicaprylyl carbonate, cetearyl isononanoate, oleyl erucate, erucyl oleate, erucyl erucate, octyldodecanol, polydecenes, squalane, dicaprylyl ether, triisostearine, butylene glycol dicaprylate, caprylic/capric triglyceride, vegetable oil, olive oil, sunflower oil, soybean oil, peanut oil, rapeseed oil, sesame oil, mustard oil, almond oil, palm oil, raw coconut oil, paraffin oil, mineral oil, flaxseed oil, palm kernel oil, caster oil, wheat germ oil, grape seed oil, thistle oil, silicon oils, lanolin oil, avocado oil and macadamia oil.

The pesticidal composition of the present disclosure specifically comprises: i) azadirachtin; and ii) at least one potassium salt of a fatty acid; and iii) at least one excipient.

The pesticidal composition of the present disclosure may be in the form of solutions, aerial sprays, directly sprayable solutions, powders, suspensions, dispersions, emulsions, oil dispersions, pastes and water dispersible granules.

The excipient used for the preparation of the composition of the present disclosure includes vehicles, alkalizing agents, acidifying agents, dispersing agents, wetting agents, binding agents, emulsifiers, defoamers, oils, wax, stabilizers and combinations thereof.

The vehicle is at least one solvent selected from the group consisting of water, ethanol, methanol, butanol, propanol, glycol, cyclohexanone, xylene, toluene, benzene, chloroform, acetone, acetonitrile, methylene chloride, dimethylformamide, hexane, hydrocarbons, ethers, esters and ketones.

The alkalizing agent is at least one selected from the group consisting of ammonia solution, ammonium carbonate, diethanolamine, monoethanolamine, potassium hydroxide, sodium bicarbonate, sodium borate, sodium carbonate, sodium hydroxide, sodium phosphate dibasic and trolamine.

The acidifying agent is selected from the group consisting of acetic acid, glacial, acetic acid, citric acid, fumaric acid, hydrochloric acid, lactic acid, maleic acid, nitric acid, phosphoric acid, propionic acid, sulfuric acid and tartaric acid.

The dispersing agent is selected from the group consisting of polyvinylpyrrolidone, polyvinylalcohol, lignosulphonates, phenyl naphthalene sulphonates, ethoxylated allcyl phenols, ethoxylated fatty acids, alkoxylated linear alcohols, polyaromatic sulfonates, sodium alkyl aryl sulfonates, glyceryl esters and maleic anhydride copolymers.

The wetting agent is selected from the group consisting of phenyl naphthalene sulphonates, alkyl naphthalene sulfonates, sodium alkyl naphthalene sulfonate, sodium salt of sulfonated alkylcarboxylate, polyoxyalkylated ethyl phenols, polyoxyethoylated fatty alcohols, polyoxyethoxylated fatty amines, lignin derivatives, alkane sulfonates, alkylbenzene sulfonates, salts of polycarboxylic acids, salts of esters of sulfosuccinic acid, alkylnaphthalenesulphonates, alkylbenzenesulfonates, alkylpolyglycol ether sulfonates, alkyl ether phosphates, alkyl ether sulphates and alkyl sulfosuccinic monoesters.

The binding agent is selected from the group consisting of starch, pregelatinized starch, gelatin, vinyl chloride, povidone, hydroxylpropyl cellulose, ethyl cellulose, xanthan gum, cellulose acetate phthalate, hydroxylpropyl methyl cellulose, polyvinyl alcohols, phenyl naphthalene sulphonate, lignin derivatives, polyvinyl pyrrolidone, polyalkyl pyrrolidone, polyethoxylated fatty acids, polyethoxylated fatty alcohols, ethylene oxide copolymer, propylene oxide copolymer, polyethylene glycols and polyethylene oxides.

The emulsifier is selected from the group consisting of alkyl polyethylene oxide, alkylphenol polyethylene oxide, sodium laureth sulphate, sodium dodecyl sulphate, alkyl alcohol, sodium lauryl sulfate, polyoxyethylene/polyoxypropylene block polymers (poloxamers), glycerols, polyglycerols, fatty acids, polyethylene glycol hydroxy stearate, polyalkyl glucosides, ceramides, polyethylene glycol/alkyl glycol copolymers, and polyethylene glycol/polyalkylene glycol ether di-block or tri-block copolymers, diacetylated monoglycerides, diethylene glycol monostearate, ethylene glycol monostearate, ethoxylated castor oil, glyceryl monooleate, propylene glycol monostearate, macrogol esters, macrogol stearate, polyoxyethylene 50 stearate, macrogol ethers, cetomacrogol 1000, lauromacrogols, nonoxynols, octoxinols, tyloxapol, polyvinyl alcohols, polysorbate, sorbitan monolaurate, sorbitan monooleate, sorbitan monopalmitate, sorbitan sesquioleate, sorbitan trioleate, sorbitan tristearate, sucrose esters, cetyl alcohol, oleyl alcohol, cetylpyridinium chloride, cetyl trimethylammonium bromide, tween 20 and tween 80.

The wax is at least one selected from the group consisting of candelilla wax, carnauba wax, bees wax, esparto grass wax, cork wax, guaruma wax, rice germ oil wax, sugarcane wax, berry wax, ouricury wax, montan wax, jojoba wax, shea butter, beeswax, shellac wax, spermaceti, wool wax, ceresin, ozokerite wax, paraffin wax, sunflower wax, lemon wax, grape fruit wax and laurel wax.

In accordance with another aspect of the present disclosure the composition is provided in the form of a kit. The kit comprises the following components:

i) component A comprising at least one substance derived from *Azadirachta indica* plant;

ii) component B comprising at least one metal salt of a fatty acid selected from the group consisting of a potassium salt of a fatty acid, a sodium salt of a fatty acid, a calcium salt of a fatty acid, a magnesium salt of a fatty acid, an aluminium salt of a fatty acid and a manganese salt of a fatty acid; and iii) at least one packaging material for packaging of the components (A) and (B).

Typically, the substance derived from *Azadirachta indica* plant includes a powder, crude, extract, oil, active constituents obtained from leaves, seeds, root, bark or any combinations thereof.

In accordance with one of the embodiments of the present disclosure the components A and/or B of the kit further comprises at least one excipient selected from the group consisting of vehicles, alkalizing agents, acidifying agents, dispersing agents, wetting agents, binding agents, emulsifiers, oils, wax, defoamers and stabilizers.

In one of the embodiment of the present disclosure the oil in the kit is at least one selected from the group consisting of isopropyl myristate, myristyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, ethylhexyl cocoate, dicaprylyl carbonate, cetearyl isononanoate, oleyl erucate, erucyl oleate, erucyl erucate, octyldodecanol, polydecenes, squalane, dicaprylyl ether, triisostearine, butylene glycol dicaprylate, caprylic/capric triglyceride, vegetable oil, olive oil, sunflower oil, soybean oil, peanut oil, rapeseed oil, sesame oil, mustard oil, almond oil, palm oil, raw coconut oil, paraffin oil, mineral oil, flaxseed oil, palm kernel oil, caster oil, wheat germ oil, grape seed oil, thistle oil, silicon oils, lanolin oil, avocado oil and macadamia oil.

In accordance with one of the embodiments of the disclosure, the substance used in the composition of the present disclosure is any variant of azadirachtin, namely azadirachtin A, azadirachtin B or any combinations thereof.

In accordance with one of the embodiments the composition is in the form of a kit, said kit comprising:
i. component X comprising azadirachtin;
ii. component Y comprising at least one compound selected from the group consisting of a potassium salt of a fatty acid, propylene glycol, and potassium hydroxide; and
iii. at least one packaging material for packaging of the components (X) and (Y).

In accordance with another aspect of the present disclosure there is provided a process for the preparation of the pesticidal composition. In one of the embodiments the process involves mixing in any order at least one substance derived from the *Azadirachta indica* plant and at least one metal salt of a fatty acid and optionally with at least one excipient.

In accordance with one of the embodiments of the present disclosure the components A and/or B of the kit further comprises at least one excipient selected from the group consisting of vehicles, alkalizing agents, acidifying agents, dispersing agents, wetting agents, binding agents, emulsifiers, oils, wax, defoamers and stabilizers.

In accordance with another aspect of the present disclosure there is provided an effective method of controlling a wide variety of insect pests such as Adelgid, ants, Aphids, armyworm, Balsam woolly adelgid, Blossom thrips on African violets, Broad mites, buck moth larvae, campylomas, Chinch bugs, Citrus rust mites, Conifer and pine needle scale, Cooley Spruce gall adelgid, cutworm, Earwig, elm leaf beetle larvae, Euonymous scale, European red mites, fleahopper, fleas, fungus gnat, Green apple aphids, Green peach, greenbug, grubs, gypsy moth eggs and larvae, Gypsy moth, Hemlock woolly adelgid, Japanese beetle, lace bugs, Leafhopper, Leafminer (Dipteran), leafroller, looper, Lygus bug, Mealy Bug, Mite, Mole crickets, Pacific mites, Pea aphid, peach twig borers, peach tree borers, Psylla, pear Psylla, pear slug (sawfly larvae), phylloxera, plant bug, powdery mildew, psyllid, Rosy Apple Aphid, Russet mites, rust mites, San Jose scale, sawfly larvae, scale, shore fly, sod webworms, spider mite, Spruce spider mite on conifers, stink bug, Tent caterpillar, Thrips, True Bugs, two spotted mites, variegated leafhoppers, walnut husk fly, Weevil, western flower Nip, Western grape aphids, White apple leafhoppers, Whitefly, Willamette mites, apple maggot, banded grape bug, black pecan aphid, blueberry maggot, cherry fruit flies, codling moth, Colorado potato beetle, dock sawfly, elm spanworm, European corn borer, European sawfly, fire worms, fruit worms, grape berry moth, grape cane borer, grape leaf folder, green fruit worm, hickory shuck worm, lygocoris bug, naval orange worm, orange tortix, oriental fruit moth, pecan nut casebearer, pine tip moth, plum curculio, red humped caterpillar, rose chafer, spanworm, spotted wing drosophila, strawberry root weevil adult, syneta beetle, western grape leaf skeletonizer, western tussock moth, black cherry aphid and asian citrus psyllid.

A method for controlling pests using the pesticidal composition of the present disclosure involves the following steps:

In the first step, a composition comprising at least one substance derived from the *Azadirachta indica* plant, at least one metal salt of a fatty acid and at least one excipient is prepared. Typically, the metal salt of a fatty acid is at least one selected from the group consisting of a potassium salt of a fatty acid, a sodium salt of a fatty acid, a calcium salt of a fatty acid, a magnesium salt of a fatty acid, an aluminium salt of a fatty acid and a manganese salt of a fatty acid. Preferably, the metal salt of a fatty acid is the potassium salt of a fatty acid.

In the next step, insects in an infested area are contacted with a pesticidal effective amount of the composition. Alternatively, a pesticidal effective amount of the composition is applied on the infested area.

In accordance with another embodiment of the present disclosure there is provided a method for controlling pests using a pesticidal kit of the present disclosure.

In accordance with one embodiment of the present disclosure the component A of said kit is first brought in contact with pests followed by application of component B.

In accordance with another embodiment of the present disclosure the component B is first brought in contact with pests followed by application of component A.

In accordance with another embodiment of the present disclosure the components A and B of said kit are applied simultaneously.

In accordance with still another embodiment of the present disclosure, the components A and B of said kit are applied separately and sequentially with pre-determined time intervals between each of the applications.

In accordance with still another embodiment of the present disclosure the component A and component B of said kit are mixed and the mixture is applied to the infested area.

The component A and component B are independently in the form selected from the group consisting of solutions, aerial sprays, directly sprayable solutions, powders, suspensions, dispersions, emulsions, oil dispersions, pastes and water dispersible granules.

The composition/kit of the present disclosure may be applied at any stage of the crop's life cycle. The composition/kit of the present disclosure is more effective when applied during the fruiting of the crop.

In accordance with another embodiment of the present disclosure the method of controlling pests involves the application of the present pesticidal composition/kit to and with soil. The soil may be of any type selected from the group consisting of alluvial soil, regur soil, red soil, laterite soil, black soil, mountain and hill soil, terai soil, desert or and soil, peat soil, sandy soil, silty soil, clay soil, loamy soil, chalky soil, artificial soil and potting soil.

In accordance with still another embodiment of the present disclosure the method of controlling pests involves the application of component A of said kit to the crop and application of component B of said kit through the soil.

In accordance with yet another embodiment of the present disclosure the method of controlling pests involves the application of component B of said kit to the crop and application of component A of said kit through soil.

The composition of the present disclosure can be applied/used in various environmental and climatic conditions of varying temperature and humidity.

The pesticidal composition or the kit of the present disclosure is useful in controlling a wide variety of insect pests on crops/vegetables/fruit/nuts/turf/ornamental/perennial plants/annuals plant selected from the group consisting of Blackberry, Blueberry, Cane berries, Currant, Elderberry, Gooseberry, Huckleberry, Loganberry, Raspberry (black and red), Strawberries, Boysenberry, Olallieberry Garlic, Leek, Onion (dry bulb, green and Welch), Shallot, Sugarbeet, Barley, Buckwheat, Corn, Millet (pearl and Proso), Oats, Popcorn, Rice, Rye, Sorghum (milo), Teosinte, Triticale, Wheat, Wild rice, Calamondin, Citrus citron, Citrus hybrids, Grapefruit, Kumquat, Lemon, Lime, Mandarin (tangerine), Orange (sour and sweet), Pummelo, Satsuma mandarin, White Sapote, Uniq Fruit, Chayote, Chinese waxgourd, Citron melon, Cucumber, Gherkin, Gourd (edible), Muskmelon, Pumpkin, Squash (summer and winter), Watermelon, Alfafla, Clover, Trefoil or Vetch, Eggplant, Groundcherry, Pepino, Pepper (including bell pepper, chili pepper, cooking pepper, pimento, sweet pepper), Tomatillo, Tomato, Allspice, Angelica, Anise (anise seed and star), Annatto (seed), Balm (lemon balm), Basil, Borage, Burnet, Camomile, Caper buds, Caraway, Caraway (black), Cardamom, Cassia bark, Cassia buds, Catnip, Celery, Celery seed, Chervil (dried), Chive, Chinese Chive, Cinnamon, Clary, Clove buds, Coriander (cilantro or Chinese parsley—leaf), Coriander (cilantro—seed), Costmary, Culantro (leaf and seed), Cumin, Curry (leaf), Dill (dillweed and seed), Fennel (common, Florence), Fenugreek, Grains of paradise, Horehound, Hyssop, Juniper berry, Lavender, Lemongrass, Lovage (leaf and seed), Mace, Marigold, Marjoram, Mustard (seed), Nasturtium, Nutmeg, Parsley (dried), Pennyroyal, Pepper (black and white), Poppy (seed), Rosemary, Rue, Saffron, Sage, Savory, Sweet bay (bay leaf), Tansy, Tarragon, Thyme, Vanilla, Wintergreen, Woodruff, Wormwood, Bean, Broad Bean, Chickpea, Guar, Jackbean, Lablab bean, Lentil, Pea, Pigeon Pea, Soybean, Sword bean, Amaranth, Arugula, Broccoli, Broccoli raab (rapini), Brussels Sprouts, Cabbage, Cauliflower, Cardoon, Cavalo broccolo, Celery, Chinese Broccoli (gai lon), Chinese Cabbage (bok choy, Napa), Chinese mustard Cabbage (gai choy), Chinese Celery, Celtuce, Chervil, Chrysanthemum (edible-leaved, Garland), Collards, Corn salad, Cress (garden, upland), Dandelion, Dock (sorrel), Endive (escarole), Fennel (florence), Kale, Kohlrabi, Lettuce (head and leaf), Mizuna, Mustard Greens, Mustard Spinach, Orach, Parsley, Purslane (garden, winter), Radicchio (red chicory), Rape Greens, Rhubarb, Spinach, Spinach (New Zealand, vine), Swiss Chard, Turnip Greens, Asparagus, Avocado, Banana, Coffee, Cocoa, Cranberry, Fig, Globe artichoke, Grape, Hops, Kiwifruit, Mango, Mushroom, Okra, Olives, Papaya, Pawpaw, Peanut, Persimmon, Pineapple, Pomegranate, Strawberry, Tea, Water chestnut, Watercress, Apple, Crabapple, Loquat, Mayhaw, Quince, Oriental Pear, or Pear (Cornice), Arracacha, Arrowroot, Artichoke (Jerusalem, Chinese), Beet (garden, sugar), Burdock (edible), Canna (edible), Carrot, Cassava (bitter and sweet), Celeriac (celery root), Chayote (root), Chervil, (turnip—rooted), Chicory, Chufa, Dasheen (taro), Ginger, Ginseng, Horseradish, Leren, Oriental Radish (daikon), Parsley (turnip—rooted), Parsnip, Potato, Radish, Rutabaga, Salsify (oyster plant, black, Spanish), Skirret, Sweet potato, Tanier, Turmeric, Turnip, Yam bean (jicama, manoic pea), Yam (true), Apricot, Chemy (sweet and tart), Nectarine, Peach, Plum (Chickasaw, Damson, Japanese), Plumcot, Prune, Almond, Beech nut, Brazil nut, Butternut, Cashew, Chestnut, Chinquapin, Filbert (hazelnut, Hickory nut, Macadamia nut (bush nut), Pecan, Walnut (black and English), Pistachios, Black Sapote, Canistel, Mamey Sapote, Mango, Sapodilla, Star Apple, Guava, Feijoa, Jaboticaba, Wax Jambu, Star Fruit, Passion Fruit, Acerola, Lychee, Longan, Spanish Lime, tangelo, Rambutan, Pulasan, Sugar Apple, Atemoya, Custard Apple, Chemmoya, llama, Soursop, Biriba Amaranthus, Aster, Azalea, Ferns, Fuschia, Caladium, Carnation, Chrysanthemum, Dahlia, Daisy, Lilies, Ivy, Ficus, Gardenia, Impatiens, Iris, Jasmine, Lilac, Marigold, Philodendron, Poinsettia, Rose, Zinnia, Ash, Birch, Cedar, Cyprus, Dogwood, Fir, Elm, Juniper, Maple, Oak, Pine, Spruce, Alfalfa, Canola, Cotton, Tobacco, Christmas Tree, Oilseed Rape, Bushberry, cucurbit, legume and Beechnut.

In accordance with the present disclosure, the pesticidal composition or the pesticidal kit controls pests which include but are not limited to Adelgid, ants, Aphids, armyworm, Balsam woolly adelgid, Blossom thrips on African violets, Broad mites, buck moth larvae, campylomas, Chinch bugs, Citrus rust mites, Conifer and pine needle scale, Cooley Spruce gall adelgid, cutworm, Earwig, elm leaf beetle larvae, Euonymous scale, European red mites, fleahopper, fleas, fungus gnat, Green apple aphids, Green peach, greenbug, grubs, gypsy moth eggs and larvae, Gypsy moth, Hemlock woolly adelgid, Japanese beetle, lace bugs, Leafhopper, Leafminer (Dipteran), leafroller, looper, Lygus bug, Mealy Bug, Mite, Mole crickets, Pacific mites, Pea aphid, peach twig borers, peach tree borers, Psylla, pear Psylla, pear slug (sawfly larvae), phylloxera, plant bug, powdery mildew, psyllid, Rosy Apple Aphid, Russet mites, rust mites, San Jose scale, sawfly larvae, scale, shore fly, sod webworms, spider mite, Spruce spider mite on conifers, stink bug, Tent caterpillar, Thrips, True Bugs, two spotted mites, variegated leafhoppers, walnut husk fly, Weevil, western flower thrip, Western grape aphids, White apple leafhoppers, Whitefly, Willamette mites, apple maggot, banded grape bug, black pecan aphid, blueberry maggot, cherry fruit flies, codling moth, Colorado potato beetle, dock sawfly, elm spanworm, European corn borer, European sawfly, fire worms, fruit worms, grape berry moth, grape cane borer, grape leaf folder, green fruit worm, hickory shuck worm, lygocoris bug, naval orange worm, orange tortix, oriental fruit moth, pecan nut casebearer, pine tip moth, plum curculio, red humped caterpillar, rose chafer, spanwonn, spotted wing drosophila, strawberry root weevil adult, syneta beetle, western grape leaf skeletonizer, western tussock moth, black cherry aphid and asian citrus psyllid.

The present disclosure is further described in light of the following examples which are set forth for illustration purpose only and not to be construed for limiting the scope of the disclosure.

EXAMPLE 1

The effect of the pesticidal composition of the present disclosure was studied to control thrips on Onion. An application of the pesticidal composition of the present disclosure was carried out by using spraying technique in the sequence provided in Table I wherein Azadirachtin was applied at a rate of 4.26 grams ai per acre whereas the potassium salt of a fatty acid was applied at a rate of 1.0% to 2.0% v/v solution per acre. The spray volume of the pesticidal composition was 35 gal/A. Onion crops were closely evaluated for thrips count. The results are provided in Table 2 and graphically represented in FIG. 1:

TABLE 1

Application sequence

| Treatment Number | Application Sequence | | | | | | |
|---|---|---|---|---|---|---|---|
| 1 | Potassium salt of a fatty acid | Potassium salt of a fatty acid | Spirotetramat | Spirotetramat | Spinetoram | Spinetoram | Formetanate hydrochloride |
| 2 | Substance derived from *Azadirachta indica* plant + Potassium salt of a fatty acid (composition of the present disclosure) | Substance derived from *Azadirachta indica* plant + Potassium salt of a fatty acid (composition of the present disclosure) | Spirotetramat | Spirotetramat | Spinetoram | Spinetoram | Formetanate hydrochloride |
| 3 | Spirotetramat + Potassium salt of a fatty acid | Spirotetramat + Potassium salt of a fatty acid | Spinetoram | Spinetoram | Formetanate hydrochloride | Methomyl | Methomyl |
| 4 | Spinetoram + Potassium salt of a fatty acid | Spinetoram + Potassium salt of a fatty acid | Spirotetramat | Spinetoram | Spinetoram | Methomyl | Methomyl |
| 5 | Abamectin | Spirotetramat | Spirotetramat | Spinetoram | Spinetoram | Methomyl | Methomyl |
| 6 | Spirotetramat | Spirotetramat | Abamectin | Abamectin | Spinetoram | Spinetoram | Methomyl |

TABLE 2

Results

| Treatment Number | Averages number of thrips per treatment Days | | | | | | | | |
|---|---|---|---|---|---|---|---|---|---|
| | 0 | 7 | 10 | 13 | 20 | 27 | 34 | 42 | 48 |
| 1. | 0.035 | 0.515 | 0.4175 | 0.72575 | 3.05 | 6.5775 | 20.35 | 39.9975 | 41.935 |
| 2. | 0.0525 | 0.55 | 0.3 | 0.75075 | 4.135 | 5.41 | 6.965 | 5.715 | 4.0025 |
| 3. | 0.035 | 0.3825 | 0.385 | 0.73325 | 3.7 | 4.615 | 13.635 | 17.1825 | 10.315 |
| 4. | 0.0325 | 0.5175 | 0.465 | 0.70075 | 3.975 | 3.565 | 6.9675 | 6.185 | 4.8825 |
| 5. | 0.0175 | 0.435 | 0.3825 | 0.64825 | 2.9325 | 6.35 | 10.5825 | 27.9475 | 24.0175 |
| 6. | 0.035 | 0.5325 | 0.5175 | 0.7015 | 3.375 | 4.9175 | 20.5825 | 37.7825 | 24.365 |

From the above results, it was observed that the treatment involving the application of the composition of the present disclosure is efficient and has long lasting effect in controlling thrips.

EXAMPLE 2

Laboratory trials were conducted to determine if a combination of a substance derived from *Azadirachta indica* plant and a potassium salt of a fatty acid exhibits synergistic effect. The knockdown effect of the substance derived from *Azadirachta indica* plant, the potassium salt of fatty acid and the combination of the substance derived from *Azadirachta indica* plant+the potassium salt of fatty acid in various concentrations was studied on green peach aphid.

Initially, radish plants were dipped in the composition shown in Table 3. The dipped plants were allowed to air dry. 20 aphids per plant were introduced. The trials were replicated 5 times. The radish plants were evaluated at an interval of 1 day, 3 days, 7 days and 14 days post treatment and the average number of surviving aphids was counted and compared with the aphid population on the untreated plants (control). The results are shown below in Table 3 and graphically represented in FIG. 2.

TABLE 3

Effect of treatment on Green Peach Aphid (*Myzus persicae*) count

| Treatment No | Composition | Concentration Ml/L | Average number of aphids per plant | | | |
|---|---|---|---|---|---|---|
| | | | 1 day | 3 days | 7 days | 14 days |
| 1 | substance derived from *Azadirachta indica* plant + potassium salt of a fatty acid | 5.0 ml/L + 2.51 ml/L (0.0148 LBs ai/acre + 0.313 LBs ai/acre) | 13.0 c | 11.8 e | 10.0 cd | 51.6 c |
| 2 | substance derived from *Azadirachta indica* plant + | 0.625 ml/L + 40.16 ml/L (0.0018 LBs | 14.2 bc | 8.8 e | 9.0 d | 46.0 c |

TABLE 3-continued

Effect of treatment on Green Peach Aphid (*Myzus persicae*) count

| | | Concentration | Average number of aphids per plant | | | |
|---|---|---|---|---|---|---|
| Treatment No | Composition | Ml/L | 1 day | 3 days | 7 days | 14 days |
| | potassium salt of a fatty acid | ai/acre + 5.022 LBs ai/acre) | | | | |
| 3 | substance derived from *Azadirachta indica* plant + potassium salt of a fatty acid | 5.0 ml/L + 40.16 ml/L (0.0148 LBs ai/acre + 5.022 LBs ai/acre) | 15.0 bc | 8.6 e | 5.0 d | 40.0 c |
| 4 | substance derived from *Azadirachta indica* plant + potassium salt of a fatty acid | 0.625 ml/L + 2.51 ml/L (0.0018 LBs ai/acre + 0.313 LBs ai/acre) | 23.6 ab | 53.0 b | 93.0 b | 283.4 b |
| 5 | potassium salt of a fatty acid | 40.16 ml/L (5.022 LBs ai/acre) | 22.8 ab | 20.4 cde | 47.4 bcd | 200.0 bc |
| 6 | potassium salt of a fatty acid | 2.51 ml/L (0.313 LBs ai/acre) | 19.0 bc | 43.0 bcd | 79.6 b | 254.2 b |
| 7 | substance derived from *Azadirachta indica* plant | 5.0 ml/L (0.0148 LBs ai/acre) | 23.2 ab | 51.2 b | 64.4 bc | 201.2 bc |
| 8 | substance derived from *Azadirachta indica* plant | 0.625 ml/L (0.0018 LBs ai/acre) | 16.0 bc | 17.6 de | 40.0 bcd | 203.0 bc |
| 9 | substance derived from *Azadirachta indica* plant | 2.5 ml/L (0.0074 LBs ai/acre) | 17.8 bc | 35.4 bcde | 66.6 b | 230.6 b |
| 10 | potassium salt of a fatty acid | 20.08 ml/L (2.511 LBs ai/acre) | 23.4 ab | 48.6 bc | 90.0 b | 333.4 ab |
| 11 | Untreated control | — | 32.2 a | 95.0 a | 172.2 a | 492.0 a |

Form the results as shown in Table 3, it is clear that the combinations of the two compounds (the substance derived from *Azadirachta indica* plant and the potassium salt of a fatty acid) are much more effective than the single treatments or the Untreated control. Further, the treatment No's 1, 2 and 3 were found to be more effective.

The observed average control (%) of aphids of each treatment was used to evaluate the data for synergistic effects using the Colby Formula (S. R. Colby, 1966). The Colby Formula (represented herein below) also called as the Abbott formula has long been recognized as dependable means of identifying synergism between two or more compounds with different modes of action.

$$E = x + y - xy/100 \quad \text{Colby's formula}$$

E: expected efficacy (%), when using the mixture of active substances A and B in the concentrations a and b x: efficacy (%) when using active substance A in the concentration a y: efficacy (%) when using active substance B in the concentration b In this particular test, the potassium salt of a fatty acid is considered as a quick acting contact knockdown insecticide and the substance derived from *Azadirachta indica* plant is a slower acting insect growth regulator. Results of this analysis are depicted in Tables 4 and 5.

The Colby Formula calculates the level of control that would be expected from each treatment and compares these values to the level of control actually measured. The ratio of % control observed over % control predicted is called the Synergy Factor (SF). A SF less than 1 indicates the compounds are antagonistic. A SF equal to 1 indicates the compounds are most likely additive while a SF greater than 1 indicates the high likelihood of synergism. When values are close to 1.0 (0.9-1.1) other factors should also be considered such as the statistical significance of differences between observed results and perhaps other test parameters.

TABLE 4

Synergistic effect (calculated using Colby formula) of the combination of the potassium salt of a fatty acid and the substance derived from *Azadirachta indica* plant in controlling Green Peach Aphid on day 3 after treatment.

| substance derived from *Azadirachta indica* plant Concentration | potassium salt of a fatty acid Concentration | % Control (Observed) | % Control (Predicted) | Synergy Factor |
|---|---|---|---|---|
| 0.625 ml/L | 2.51 ml/L | 30.37 | 86.63 | 0.35 |
| 0.625 ml/L | 40.16 ml/L | 90.53 | 93.68 | 0.97 |
| 5.0 ml/L | 2.51 ml/L | 87.77 | 62.57 | 1.40 |
| 5.0 ml/L | 40.16 ml/L | 89.33 | 82.32 | 1.09 |
| 0.625 ml/L | — | 75.90 | — | — |
| 5.0 ml/L | — | 32.54 | — | — |
| — | 2.51 ml/L | 44.51 | — | — |
| — | 40.16 ml/L | 73.79 | — | — |

TABLE 5

Synergistic effect (calculated using Colby formula) of the combination of the potassium salt of a fatty acid and the substance derived from *Azadirachta indica* plant in controlling Green Peach Aphid on day 14 after treatment.

| substance derived from *Azadirachta indica* plant Concentration | potassium salt of a fatty acid Concentration | % Control (Observed) | % Control (Predicted) | Synergy Factor |
|---|---|---|---|---|
| 0.625 ml/L | 2.51 ml/L | 40.95 | 76.10 | 0.54 |
| 0.625 ml/L | 40.16 ml/L | 92.14 | 82.94 | 1.11 |

TABLE 5-continued

Synergistic effect (calculated using Colby formula) of the combination of the potassium salt of a fatty acid and the substance derived from Azadirachta indica plant in controlling Green Peach Aphid on day 14 after treatment.

| substance derived from Azadirachta indica plant Concentration | potassium salt of a fatty acid Concentration | % Control (Observed) | % Control (Predicted) | Synergy Factor |
|---|---|---|---|---|
| 5.0 ml/L | 2.51 ml/L | 90.49 | 76.86 | 1.18 |
| 5.0 ml/L | 40.16 ml/L | 89.07 | 83.48 | 1.07 |
| 0.625 ml/L | — | 57.32 | — | — |
| 5.0 ml/L | — | 58.67 | — | — |
| — | 2.51 ml/L | 44.01 | — | — |
| — | 40.16 ml/L | 60.02 | — | — |

In view of the above results, it can be concluded that the synergistic effect is observed for the combination of the substance derived from Azadirachta indica plant and the potassium salt of a fatty acid at 2:1 ratio.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "a", "at least" or "at least one" suggests the use of one or more elements or ingredients or quantities, as the use may be in the embodiment of the disclosure to achieve one or more of the desired objects or results.

The numerical values given for various physical parameters, dimensions and quantities are only approximate values and it is envisaged that the values higher or lower than the numerical value assigned to the physical parameters, dimensions and quantities fall within the scope of the disclosure and the claims unless there is a statement in the specification to the contrary.

While certain embodiments of the inventions have been described, these embodiments have been presented by way of examples only, and are not intended to limit the scope of the disclosure. Variations or modifications in the process or product or combination of this invention, within the scope of the disclosure, may occur to those skilled in the art upon reviewing the disclosure herein. Such variations or modifications are well within the spirit of this disclosure. The accompanying claims and their equivalents are intended to cover such forms or modifications as would fall within the scope and spirit of the disclosure.

The invention claimed is:

1. A synergistic pesticidal composition adapted for the control of undesired insect pests comprising:
  i. at least one substance derived from Azadirachta indica plant;
  ii. at least one metal salt of a fatty acid; and
  iii. at least one excipient,
  wherein the i. at least one substance derived from Azadirachta indica plant and the ii. at least one metal salt of a fatty acid are present in an a.i. weight ratio range of about 1:21.14-2790,
  and, wherein the said composition exhibits a Synergy Factor of greater than 1 according to Colby's formula.

2. The syngeristic pesticidal composition according to claim 1, wherein the substance is selected from the group comprising powder, extract and oil derived from Azadirachta indica plant material and azadirachtins.

3. The synergistic pesticidal composition according to claim 1, wherein the metal salt of a fatty acid is at least one selected from the group consisting of a potassium salt of a fatty acid, a sodium salt of a fatty acid, a calcium salt of a fatty acid, a magnesium salt of a fatty acid, an aluminium salt of a fatty acid and a manganese salt of a fatty acid, preferably, a potassium salt of a fatty acid.

4. The synergistic pesticidal composition according to claim 1, wherein the a.i. ratio of the substance derived from Azadirachta indica plant and the metal salt of a fatty acid ranges is in the range of about 1:21.14 -339.

5. The synergistic pesticidal composition according to claim 1, wherein the amount of the metal salt of a fatty acid ranges between 0.01 w/w % and 30.0 w/w %.

6. The synergistic pesticidal composition according to claim 1, further comprises at least one oil selected from the group consisting of isopropyl myristate, myristyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, ethylhexyl cocoate, dicaprylyl carbonate, cetearyl isononanoate, oleyl erucate, erucyl oleate, erucyl erucate, octyldodecanol, polydecenes, squalane, dicaprylyl ether, triisostearine, butylene glycol dicaprylate, caprylic/capric triglyceride, vegetable oil, olive oil, sunflower oil, soybean oil, peanut oil, rapeseed oil, sesame oil, mustard oil, almond oil, palm oil, raw coconut oil, paraffin oil, mineral oil, flaxseed oil, palm kernel oil, caster oil, wheat germ oil, grape seed oil, thistle oil, silicon oils, lanolin oil, avocado oil and macadamia oil.

7. The synergistic pesticidal composition according to claim 1, wherein the excipient is at least one selected from the group consisting of vehicles, alkalizing agents, acidifying agents, dispersing agents, wetting agents, binding agents, emulsifiers, defoamers, wax and stabilizers.

8. The synergistic pesticidal composition according to claim 1, wherein the composition is in the form selected from the group consisting of aerial sprays, directly sprayable solutions, powders, suspensions, dispersions, emulsions, oil dispersions, pastes and water dispersible granules.

9. A method for controlling pests; said method comprising the following steps:
  i. preparing a composition composition according to claim 1; and
  ii. applying a pestically effective amount of said composition to a plant or crop.

10. The method as claimed in claim 9, wherein the metal salt of a fatty acid is at least one selected from the group consisting of a potassium salt of a fatty acid, a sodium salt of a fatty acid, a calcium salt of a fatty acid, a magnesium salt of a fatty acid, an aluminium salt of a fatty acid and a manganese salt of a fatty acid, preferably, a potassium salt of a fatty acid.

11. A kit comprising;
  i. component A comprising at least one substance derived from Azadirachta indica plant;
  ii. component B comprising at least one metal salt of a fatty acid selected from the group consisting of a potassium salt of a fatty acid, a sodium salt of a fatty acid, a calcium salt of a fatty acid, a magnesium salt of a fatty acid, an aluminium salt of a fatty acid and a manganese salt of a fatty acid; and
  iii. at least one packaging material for packaging of the components (A) and (B),
  wherein the mixtures of the components A and B have an a.i. weight ratio of component A to component B in a weight ratio range of about 1:21.1-2790.

12. The kit according to claim 11 further comprises at least one excipient selected from the group consisting of vehicles, alkalizing agents, acidifying agents, dispersing agents, wetting agents, binding agents, emulsifiers, defoamers, oils, wax and stabilizers.

13. The kit according to claim 11, wherein the substance is selected from the group comprising powder, extract and oil derived from *Azadirachta indica* plant material and azadirachtins.

14. The kit according to claim 12, wherein the oil is at least one oil selected from the group consisting of: isopropyl myristate, myristyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, ethylhexyl cocoate, dicaprylyl carbonate, cetearyl isononanoate, oleyl erucate, erucyl oleate, erucyl erucate, octyldodecanol, polydecenes, squalane, dicaprylyl ether, tri-isostearine, butylene glycol dicaprylate, caprylic/capric triglyceride, vegetable oil, olive oil, sunflower oil, soybean oil, peanut oil, rapeseed oil, sesame oil, mustard oil, almond oil, palm oil, raw coconut oil, paraffin oil, mineral oil, flaxseed oil, palm kernel oil, caster oil, wheat germ oil, grape seed oil, thistle oil, silicon oils, lanolin oil, avocado oil and macadamia oil.

15. A method for controlling pests using the kit as claimed in claim 11; said method comprising applying the components by at least one technique selected from the group consisting of applying the component A before the application of the component B, applying the component A after the application of the component B, simultaneous application of the components A and B and combining the components A and B before the application.

16. A method for controlling pests using the pesticidal composition as claimed in claim 1, said method comprising controlling a wide variety of insect pests on crops/vegetables/fruit/nuts/turf/ornamental/perennial plants/annuals plant selected from the group consisting of Blackberry, Blueberry, Cane berries, Currant, Elderberry, Gooseberry, Huckleberry, Loganberry, Raspberry (black and red), Strawberries, Boysenberry, Olallieberry Garlic, Leek, Onion (dry bulb, green and Welch), Shallot, Sugarbeet, Barley, Buckwheat, Corn, Millet (pearl and Proso), Oats, Popcorn, Rice, Rye, Sorghum (milo), Teosinte, Triticale, Wheat, Wild rice, Calamondin, Citrus citron, Citrus hybrids, Grapefruit, Kumquat, Lemon, Lime, Mandarin (tangerine), Orange (sour and sweet), Pummelo, Satsuma mandarin, White Sapote, Uniq Fruit, Chayote, Chinese waxgourd, Citron melon, Cucumber, Gherkin, Gourd (edible), Muskmelon, Pumpkin, Squash (summer and winter), Watermelon, Alfafla, Clover, Trefoil or Vetch, Eggplant, Groundcherry, Pepino, Pepper (including bell pepper, chili pepper, cooking pepper, pimento, sweet pepper), Tomatillo, Tomato, Allspice, Angelica, Anise (anise seed and star), Annatto (seed), Balm (lemon balm), Basil, Borage, Burnet, Camomile, Caper buds, Caraway, Caraway (black), Cardamom, Cassia bark, Cassia buds, Catnip, Celery, Celery seed, Chervil (dried), Chive, Chinese Chive, Cinnamon, Clary, Clove buds, Coriander (cilantro or Chinese parsley—leaf), Coriander (cilantro—seed), Costmary, Culantro (leaf and seed), Cumin, Curry (leaf), Dill (dillweed and seed), Fennel (common, Florence), Fenugreek, Grains of paradise, Horehound, Hyssop, Juniper berry, Lavender, Lemongrass, Lovage (leaf and seed), Mace, Marigold, Marjoram, Mustard (seed), Nasturtium, Nutmeg, Parsley (dried), Pennyroyal, Pepper (black and white), Poppy (seed), Rosemary, Rue, Saffron, Sage, Savory, Sweet bay (bay leaf), Tansy, Tarragon, Thyme, Vanilla, Wintergreen, Woodruff, Wormwood, Bean, Broad Bean, Chickpea, Guar, Jackbean, Lablab bean, Lentil, Pea, Pigeon Pea, Soybean, Sword bean, Amaranth, Arugula, Broccoli, Broccoli raab (rapini), Brussels Sprouts, Cabbage, Cauliflower, Cardoon, Cavalo broccolo, Celery, Chinese Broccoli (gai lon), Chinese Cabbage (bok Choy, Napa), Chinese mustard Cabbage (gai choy), Chinese Celery, Celtuce, Chervil, Chrysanthemum (edible—leaved, Garland), Collards, Corn salad, Cress (garden, upland), Dandelion, Dock (sorrel), Endive (escarole), Fennel (florence), Kale, Kohlrabi, Lettuce (head and leaf), Mizuna, Mustard Greens, Mustard Spinach, Orach, Parsley, Purslane (garden, winter), Radicchio (red chicory), Rape Greens, Rhubarb, Spinach, Spinach (New Zealand, vine), Swiss Chard, Turnip Greens, Asparagus, Avocado, Banana, Coffee, Cocoa, Cranberry, Fig, Globe artichoke, Grape, Hops, Kiwifruit, Mango, Mushroom, Okra, Olives, Papaya, Pawpaw, Peanut, Persimmon, Pineapple, Pomegranate, Strawberry, Tea, Water chestnut, Watercress, Apple, Crabapple, Loquat, Mayhaw, Quince, Oriental Pear, or Pear (Cornice), Arracacha, Arrowroot, Artichoke (Jerusalem, Chinese), Beet (garden, sugar), Burdock (edible), Canna (edible), Carrot, Cassava (bitter and sweet), Celeriac (celery root), Chayote (root), Chervil, (turnip—rooted), Chicory, Chufa, Dasheen (taro), Ginger, Ginseng, Horseradish, Leren, Oriental Radish (daikon), Parsley (turnip—rooted), Parsnip, Potato, Radish, Rutabaga, Salsify (oyster plant, black, Spanish), Skirret, Sweet potato, Tanier, Turmeric, Turnip, Yam bean (jicama, manoic pea), Yam (true), Apricot, Cherry (sweet and tart), Nectarine, Peach, Plum (Chickasaw, Damson, Japanese), Plumcot, Prune, Almond, Beech nut, Brazil nut, Butternut, Cashew, Chestnut, Chinquapin, Filbert (hazelnut, Hickory nut, Macadamia nut (bush nut), Pecan, Walnut (black and English), Pistachios, Black Sapote, Canistel, Mamey Sapote, Mango, Sapodilla, Star Apple, Guava, Feijoa, Jaboticaba, Wax Jambu, Star Fruit, Passion Fruit, Acerola, Lychee, Longan, Spanish Lime, tangelo, Rambutan, Pulasan, Sugar Apple, Atemoya, Custard Apple, Chemmoya, llama, Soursop, Biriba, Amaranthus, Aster, Azalea, Ferns, Fuschia, Caladium, Carnation, Chrysanthemum, Dahlia, Daisy, Lilies, Ivy, Ficus, Gardenia, Impatiens, Iris, Jasmine, Lilac, Marigold, Philodendron, Poinsettia, Rose, Zinnia, Ash, Birch, Cedar, Cyprus, Dogwood, Fir, Elm, Juniper, Maple, Oak, Pine, Spruce, Alfalfa, Canola, Cotton, Tobacco, Christmas Tree, Oilseed Rape, Bushberry, cucurbit, legume and Beechnut.

17. A method for controlling pests using the pesticidal composition as claimed in claim 1, comprising controlling at least one pest selected from the group consisting of Adelgid, ants, Aphids, armyworm, Balsam woolly adelgid, Blossom thrips on African violets, Broad mites, buck moth larvae, campylomas, Chinch bugs, Citrus rust mites, Conifer and pine needle scale, Cooley Spruce gall adelgid, cutworm, Earwig, elm leaf beetle larvae, Euonymous scale, European red mites, fleahopper, fleas, fungus gnat, Green apple aphids, Green peach, greenbug, grubs, gypsy moth eggs and larvae, Gypsy moth, Hemlock woolly adelgid, Japanese beetle, lace bugs, Leafhopper, Leafminer (Dipteran), leafroller, looper, Lygus bug, Mealy Bug, Mite, Mole crickets, Pacific mites, Pea aphid, peach twig borers, peach tree borers, Psylla, pear Psylla, pear slug (sawfly larvae), phylloxera, plant bug, powdery mildew, psyllid, Rosy Apple Aphid, Russet mites, rust mites, San Jose scale, sawfly larvae, scale, shore fly, sod webworms, spider mite, Spruce spider mite on conifers, stink bug, Tent caterpillar, Thrips, True Bugs, two spotted mites, variegated leafhoppers, walnut husk fly, Weevil, western flower thrip, Western grape aphids, White apple leafhoppers, Whitefly, Willamette mites, apple maggot, banded grape bug, black pecan aphid, blueberry maggot, cherry fruit flies, codling moth, Colorado potato beetle, dock sawfly, elm spanworm, European corn borer, European sawfly, fire worms, fruit worms, grape berry moth, grape cane borer, grape leaf folder, green fruit worm, hickory shuck worm, lygocoris bug, naval orange worm, orange tortix, oriental fruit moth, pecan nut casebearer, pine tip moth, plum curculio, red humped caterpillar, rose chafer, spanworm, spotted wing drosophila, strawberry root weevil adult, syneta beetle, western grape leaf skeletonizer, western tussock moth, black cherry aphid and asian citrus psyllid.

18. A method for controlling pests using the kit as claimed in claim 11, comprising controlling a wide variety of insect pests on crops/vegetables/fruit/nuts/turf/ornamental/perennial plants/annuals plant selected from the group consisting of Blackberry, Blueberry, Cane berries, Currant, Elderberry, Gooseberry, Huckleberry, Loganberry, Raspberry (black and red), Strawberries, Boysenberry, Olallieberry Garlic, Leek, Onion (dry bulb, green and Welch), Shallot, Sugarbeet, Barley, Buckwheat, Corn, Millet (pearl and Proso), Oats, Popcorn, Rice, Rye, Sorghum (milo), Teosinte, Triticale, Wheat, Wild rice, Calamondin, Citrus citron, Citrus hybrids, Grapefruit, Kumquat, Lemon, Lime, Mandarin (tangerine), Orange (sour and sweet), Pummelo, Satsuma mandarin, White Sapote, Uniq Fruit, Chayote, Chinese waxgourd, Citron melon, Cucumber, Gherkin, Gourd (edible), Muskmelon, Pumpkin, Squash (summer and winter), Watermelon, Alfafla, Clover, Trefoil or Vetch, Eggplant, Groundcherry, Pepino, Pepper (including bell pepper, chili pepper, cooking pepper, pimento, sweet pepper), Tomatillo, Tomato, Allspice, Angelica, Anise (anise seed and star), Annatto (seed), Balm (lemon balm), Basil, Borage, Burnet, Camomile, Caper buds, Caraway, Caraway (black), Cardamom, Cassia bark, Cassia buds, Catnip, Celery, Celery seed, Chervil (dried), Chive, Chinese Chive, Cinnamon, Clary, Clove buds, Coriander (cilantro or Chinese parsley—leaf), Coriander (cilantro—seed), Costmary, Culantro (leaf and seed), Cumin, Curry (leaf), Dill (dillweed and seed), Fennel (common, Florence), Fenugreek, Grains of paradise, Horehound, Hyssop, Juniper berry, Lavender, Lemongrass, Lovage (leaf and seed), Mace, Marigold, Marjoram, Mustard (seed), Nasturtium, Nutmeg, Parsley (dried), Pennyroyal, Pepper (black and white), Poppy (seed), Rosemary, Rue, Saffron, Sage, Savory, Sweet bay (bay leaf), Tansy, Tarragon, Thyme, Vanilla, Wintergreen, Woodruff, Wormwood, Bean, Broad Bean, Chickpea, Guar, Jackbean, Lablab bean, Lentil, Pea, Pigeon Pea, Soybean, Sword bean, Amaranth, Arugula, Broccoli, Broccoli raab (rapine, Brussels Sprouts, Cabbage, Cauliflower, Cardoon, Cavalo broccolo, Celery, Chinese Broccoli (gai Ion), Chinese Cabbage (bok choy, Napa), Chinese mustard Cabbage (gai choy), Chinese Celery, Celtuce, Chervil, Chrysanthemum (edible—leaved, Garland), Collards, Corn salad, Cress (garden, upland), Dandelion, Dock (sorrel), Endive (escarole), Fennel (florence), Kale, Kohlrabi, Lettuce (head and leaf), Mizuna, Mustard Greens, Mustard Spinach, Orach, Parsley, Purslane (garden, winter), Radicchio (red chicory), Rape Greens, Rhubarb, Spinach, Spinach (New Zealand, vine), Swiss Chard, Turnip Greens, Asparagus, Avocado, Banana, Coffee, Cocoa, Cranberry, Fig, Globe artichoke, Grape, Hops, Kiwifruit, Mango, Mushroom, Okra, Olives, Papaya, Pawpaw, Peanut, Persimmon, Pineapple, Pomegranate, Strawberry, Tea, Water chestnut, Watercress, Apple, Crabapple, Loquat, Mayhaw, Quince, Oriental Pear, or Pear (Cornice), Arracacha, Arrowroot, Artichoke (Jerusalem, Chinese), Beet (garden, sugar), Burdock (edible), Canna (edible), Carrot, Cassava (bitter and sweet), Celeriac (celery root), Chayote (root), Chervil, (turnip—rooted), Chicory, Chufa, Dasheen (taro), Ginger, Ginseng, Horseradish, Leren, Oriental Radish (daikon), Parsley (turnip—rooted), Parsnip, Potato, Radish, Rutabaga, Salsify (oyster plant, black, Spanish), Skirret, Sweet potato, Tanier, Turmeric, Turnip, Yam bean (jicama, manoic pea), Yarn (true), Apricot, Chemy (sweet and tart), Nectarine, Peach, Plum (Chickasaw, Damson, Japanese), Plumcot, Prune, Almond, Beech nut, Brazil nut, Butternut, Cashew, Chestnut, Chinquapin, Filbert (hazelnut, Hickory nut, Macadamia nut (bush nut), Pecan, Walnut (black and English), Pistachios, Black Sapote, Canistel, Mamey Sapote, Mango, Sapodilla, Star Apple, Guava, Feijoa, Jaboticaba, Wax Jambu, Star Fruit, Passion Fruit, Acerola, Lychee, Longan, Spanish Lime, tangelo, Rambutan, Pulasan, Sugar Apple, Atemoya, Custard Apple, Chemmoya, llama, Soursop, Biriba, Amaranthus, Aster, Azalea, Ferns, Fuschia, Caladium, Carnation, Chrysanthemum, Dahlia, Daisy, Lilies, Ivy, Ficus, Gardenia, Impatiens, Iris, Jasmine, Lilac, Marigold, Philodendron, Poinsettia, Rose, Zinnia, Ash, Birch, Cedar, Cyprus, Dogwood, Fir, Elm, Juniper, Maple, Oak, Pine, Spruce, Alfalfa, Canola, Cotton, Tobacco, Christmas Tree, Oilseed Rape, Bushberry, cucurbit, legume and Beechnut.

19. A method for controlling pests using the kit as claimed in claim 11, comprising controlling at least one pest selected from the group consisting of Adelgid, ants, Aphids, armyworm, Balsam woolly adelgid, Blossom thrips on African violets, Broad mites, buck moth larvae, campylomas, Chinch bugs, Citrus rust mites, Conifer and pine needle scale, Cooley Spruce gall adelgid, cutworm, Earwig, elm leaf beetle larvae, Euonymous scale, European red mites, fleahopper, fleas, fungus gnat, Green apple aphids, Green peach, greenbug, grubs, gypsy moth eggs and larvae, Gypsy moth, Hemlock woolly adelgid, Japanese beetle, lace bugs, Leafhopper, Leafminer (Dipteran), leafroller, looper, Lygus bug, Mealy Bug, Mite, Mole crickets, Pacific mites, Pea aphid, peach twig borers, peach tree borers, Psylla, pear Psylla, pear slug (sawfly larvae), phylloxera, plant bug, powdery mildew, psyllid, Rosy Apple Aphid, Russet mites, rust mites, San Jose scale, sawfly larvae, scale, shore fly, sod webworms, spider mite, Spruce spider mite on conifers, stink bug, Tent caterpillar, Thrips, True Bugs, two spotted mites, variegated leafhoppers, walnut husk fly, Weevil, western flower thrip, Western grape aphids, White apple leafhoppers, Whitefly, Willamette mites, apple maggot, banded grape bug, black pecan aphid, blueberry maggot, cherry fruit flies, codling moth, Colorado potato beetle, dock sawfly, elm spanworm, European corn borer, European sawfly, fire worms, fruit worms, grape berry moth, grape cane borer, grape leaf folder, green fruit worm, hickory shuck worm, lygocoris bug, naval orange worm, orange tortix, oriental fruit moth, pecan nut casebearer, pine tip moth, plum curculio, red humped caterpillar, rose chafer, spanworm, spotted wing drosophila, strawberry root weevil adult, syneta beetle, western grape leaf skeletonizer, western tussock moth, black cherry aphid and asian citrus psyllid.

20. The synergistic pesticidal composition according to claim 4, wherein the a.i. ratio of the substance derived from *Azadirachta indica* plant and the metal salt of a fatty acid is in the range of about 1:21.14-173.8.

21. The synergistic pesticidal composition according to claim 1, wherein the composition when applied to a plant or plant part at a specific application rate exhibits a greater degree of control of undesired insect pests subsequent to application as compared to (a) a like pesticidal composition but in which the substance derived from *Azadirachta indica* plant present in the synergistic pesticidal composition is omitted, and/or (b) a like pesticidal composition but in which the metal salt of the fatty acid present in the synergistic pesticidal composition is omitted.

22. The synergistic pesticidal composition according to claim 1, in which the at least one metal salt of a fatty acid is a potassium salt of C4 to C28 fatty acid.

23. The synergistic pesticidal composition according to claim 1 which comprises, per liter of the said composition:
   i. at least 0.5 ml/L of at least one substance derived from *Azadirachta indica* plant;
   ii. at least 2.51 ml/L of at least one metal salt of a fatty acid; and
   iii. at least one excipient.

24. The synergistic pesticidal composition according to claim 23 wherein the at least one substance derived from *Azadirachta indica* plant is azadirachtin A and/or azadirachtin B.

25. A synergistic pesticidal composition effective in the for the control of undesired insect pests comprising:
   i. at least one substance derived from *Azadirachta indica* plant;
   ii. at least one metal salt of a fatty acid; and
   iii. at least one excipient,
   the said composition exhibits a Synergy Factor of greater than 1.00 according to Colby's Formula.

* * * * *